US011957843B2

United States Patent
Fang et al.

(10) Patent No.: US 11,957,843 B2
(45) Date of Patent: Apr. 16, 2024

(54) CONNECTOR AND SEAL USED THEREFOR AND ANESTHESIA MACHINE USING THE CONNECTOR

(71) Applicant: GE Precision Healthcare LLC, Wauwatosa, WI (US)

(72) Inventors: Hui Fang, Jiangsu (CN); Bing Li, Jiangsu (CN); Scott A. Inman, Madison, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 719 days.

(21) Appl. No.: 16/935,825

(22) Filed: Jul. 22, 2020

(65) Prior Publication Data
US 2021/0052843 A1 Feb. 25, 2021

(30) Foreign Application Priority Data
Aug. 23, 2019 (CN) .......................... 201921384922.1

(51) Int. Cl.
*A61M 16/08* (2006.01)
*A61M 16/01* (2006.01)
*A61M 16/22* (2006.01)
*F16J 15/02* (2006.01)
*F16L 21/03* (2006.01)

(52) U.S. Cl.
CPC ........ *A61M 16/0816* (2013.01); *A61M 16/01* (2013.01); *A61M 16/22* (2013.01); *F16J 15/025* (2013.01); *F16L 21/03* (2013.01)

(58) Field of Classification Search
CPC ... A61M 16/01; A61M 16/22; Y10S 277/918; F16L 21/025; F16J 15/3268; F16J 15/02; F16J 15/025; F16J 15/3248; F16J 15/52
See application file for complete search history.

(56) References Cited

U.S. PATENT DOCUMENTS 3,707,965 A * 1/1973 Guzay ................... A61M 16/22
422/295
5,199,750 A * 4/1993 Yang ..................... F16L 21/025
285/344

(Continued)

FOREIGN PATENT DOCUMENTS

EP 2282098 A2 * 2/2011 ............ F16L 21/025
EP 2052754 B1 6/2018

*Primary Examiner* — Samchuan C Yao
*Assistant Examiner* — Tina Zhang
(74) *Attorney, Agent, or Firm* — Fletcher Yoder P.C.

(57) ABSTRACT

A connector for connecting with an absorber canister includes a first connection port for detachably communicating with an input port of the absorber canister; a second connection port for detachably communicating with an output port of the absorber canister; and a seal. The seal being sleeved on a sidewall of at least one connection port of the first connection port and the second connection port, and the seal including: an annular ring positioned on an outer sidewall of the at least one connection port; a guide chamfer portion, the guide chamfer portion being annular and extending obliquely from a bottom of the annular ring towards an interior of the at least one connection port; and a lip, the lip being annular and extending from an end portion of the guide chamfer portion in a direction towards or away from the annular ring.

4 Claims, 10 Drawing Sheets

(56) References Cited

U.S. PATENT DOCUMENTS

| | | | | |
|---|---|---|---|---|
| 5,568,910 | A | * | 10/1996 | Koehler .............. A61M 16/208 |
| | | | | 251/83 |
| 7,850,765 | B2 | * | 12/2010 | Kleinschmidt ... A61M 16/0816 |
| | | | | 96/147 |
| 8,297,660 | B2 | | 10/2012 | Rösch |
| 2005/0023772 | A1 | * | 2/2005 | England ................ F16J 15/025 |
| | | | | 277/628 |
| 2006/0130839 | A1 | * | 6/2006 | Bassovitch ....... A61M 16/0045 |
| | | | | 128/914 |
| 2013/0147126 | A1 | * | 6/2013 | Sato .................... F16J 15/3212 |
| | | | | 277/591 |

\* cited by examiner

CONNECTOR AND SEAL USED THEREFOR AND ANESTHESIA MACHINE USING THE CONNECTOR

CROSS-REFERENCE TO RELATED APPLICATIONS

This application claims the benefit of Chinese Patent Application No. 201921384922.1 filed on Aug. 23, 2019, the disclosure of which is herein incorporated by reference in its entirety.

TECHNICAL FIELD

The present utility model relates to an anesthesia machine, and in particular, to a connector for connecting with an absorber canister in a breathing circuit of an anesthesia machine, and a seal used for the connector.

BACKGROUND

A breathing circuit is a combined gas flow apparatus connected between an anesthesia machine and a patient, and is an essential part of an anesthesia machine. The breathing circuit delivers an anesthesia mixed gas containing fresh oxygen to the patient and receives a mixed gas containing carbon dioxide exhaled by the patient, thus achieving normal exchange of oxygen and carbon dioxide gases.

A breathing circuit of an anesthesia machine is usually mounted with an absorber canister, where soda lime contained therein is used to absorb the carbon dioxide gas exhaled by the patient. An absorber canister has two ports: an input port and an output port. The carbon dioxide gas exhaled by the patient enters the absorber canister from the input port. The soda lime (mainly composed of calcium hydroxide and sodium hydroxide) contained in the absorber canister absorbs carbon dioxide through chemical reaction, and at the same time releases water and heat. The mixed gas generated by the reaction, such as $CaCO_3$ and $Na_2CO_3$, is discharged from the absorber canister through the output port. When the absorption capacity of the soda lime contained in the absorber canister is exhausted, it is necessary to replace the absorber canister. The replacement involves detach the old absorber canister and mount a new absorber canister (which contains fresh soda lime).

In order to facilitate the replacement of the absorber canister, especially as the absorber canister needs to be replaced quickly in the middle of an operation, a connector is usually provided between the absorber canister and the main body of the breathing circuit of the anesthesia machine. The connector has a connection port in communication with the main body of the breathing circuit of the anesthesia machine, and furthermore has connection ports matching the input port and the output port of the absorber canister, allowing detachable communication with the absorber canister.

A seal is usually mounted on the connector. The seal is used for sealing the gas flow between the port of the absorber canister and the port of the connector when the port of the absorber canister is inserted into the port of the connector, thus preventing the gas in the breathing circuit of the anesthesia machine from leaking into the operating room. In the prior art, the seal usually adopts an O-ring. An O-ring is a seal having an O-shaped cross-section, and is usually designed to have a certain radial thickness and axial height to ensure the sealing effect. However, the use of the O-ring seal between the port of the connector and the port of the absorber canister has the following defects:

(1) The annular portion of the O-ring seal is solid. Even if the O-ring deal is made of a material with good resilience, its radial deformable range is quite limited. Therefore, the inner diameter of the O-ring seal is not easy to be too small compared with the outer diameter of the absorber canister; otherwise, it will prevent the port of the absorber canister from being quickly inserted into the port of the connector. At the meantime, if the inner diameter of the O-ring seal is too large, the sealing effect will be compromised.

(2) The O-ring seal achieves the sealing effect as its inner surface is closely attached to the outer sidewall of the port of the absorber canister. It can be understood that a greater axial height of the O-ring seal will result in a greater contact area between the inner surface of the seal and the outer sidewall of the port of the absorber canister, thus providing a better sealing effect. But on the other hand, the greater contact area between the inner surface of the seal and the outer sidewall of the port of the absorber canister will result in a greater resistance as the port of the absorber canister is inserted into the O-ring seal. Therefore, the O-ring seal with a large axial height will generate a large frictional resistance, preventing the port of the absorber canister from being quickly inserted into the port of the connector.

(3) The soda lime in the absorber canister contains tiny powder particles. During use, these powder particles will come into contact with the seal and the port of the absorber canister with the flow of gas and remain on the inner surface of the seal and the outer sidewall of the port of the absorber canister. As the powder accumulates, the resultant frictional resistance when the absorber canister is inserted into the seal will be increase over time. If an operator does not remove the accumulated powder in time, the port of the absorber canister will be prevented from being quickly inserted into the port of the connector. The carbon dioxide gas in the main body of the breathing circuit of the anesthesia machine may thus flow directly to an inhalation port of the patient, resulting in an increase in inhaled carbon dioxide $FiCO_2$.

(4) Since the absorber canister is detached and mounted repeatedly, the inner surface of the O-ring seal in contact with the port of the absorber canister is easily worn. After a period of wear, the radial thickness of the O-ring seal becomes thinner and the sealing effect becomes poor, and the seal needs to be replaced frequently.

(5) When the port of the absorber canister is inserted into the port of the connector, the operator needs to align the port of the absorber canister to the O-ring seal as much as possible, because a large deviation can impede the quick insertion of the port of the absorber canister into the port of the connector.

SUMMARY

An objective of the present utility model is to solve one or more problems existing in the prior art.

According to a first aspect of the present utility model, a connector for connecting with an absorber canister is provided, the connector comprising: a first connection port for detachably communicating with an input port of the absorber canister; a second connection port for detachably communicating with an output port of the absorber canister; and a seal, the seal being disposed on an inner sidewall of the at least one connection port of the first connection port and the second connection port. The seal comprises: an annular ring positioned on the inner sidewall of the at least one connection port; and at least one lip, the at least one lip being annular and extending from an inner side of the annular ring in a direction away from the annular ring. wherein when the absorber canister is in communication with the connector, a lower surface of the at least one lip of the seal contacts an outer sidewall of at least one port of the input port and the output port to form an annular contact surface, the width of the annular contact surface being greater than the thickness of a root portion of the at least one lip.

In at least one embodiment of the first aspect of the present utility model, the width of the annular contact surface is between 120% and 200% of the thickness of the root portion of the at least one lip.

In at least one embodiment of the first aspect of the present utility model, the width of the annular contact surface is between 140% and 180% of the thickness of the root portion of the at least one lip.

In at least one embodiment of the first aspect of the present utility model, the width of the annular contact surface is about 160% of the thickness of the root portion of the at least one lip.

In at least one embodiment of the first aspect of the present utility model, the at least one lip is made of a resilient material and the thickness of the at least one lip tapers from the root portion to an end portion.

In at least one embodiment of the first aspect of the present utility model, the seal comprises only one lip, and the one lip is disposed near a middle portion in a height direction of the annular ring.

In at least one embodiment of the first aspect of the present utility model, the seal comprises a plurality of lips, and the plurality of lips are distributed in a height direction of the annular ring.

According to a second aspect of the present utility model, a connector for connecting with an absorber canister is provided, the connector comprising: a first connection port for detachably communicating with an input port of the absorber canister; a second connection port for detachably communicating with an output port of the absorber canister; and a seal, the seal being sleeved on a sidewall of at least one connection port of the first connection port and the second connection port. The seal comprises: an annular ring positioned on an outer sidewall of the at least one connection port; a guide chamfer portion, the guide chamfer portion being annular and extending obliquely from a bottom of the annular ring towards an interior of the at least one connection port; and a lip, the lip being annular and extending from an end portion of the guide chamfer portion in a direction towards or away from the annular ring. wherein an annular hollow portion is formed between the annular ring and the guide chamfer portion, and the sidewall of the at least one connection port is positioned in the hollow portion.

In at least one embodiment of the second aspect of the present utility model, the seal further comprises a bend, the bend extending substantially in a radial direction inwards from a top portion of the annular ring.

In at least one embodiment of the second aspect of the present utility model, the lip extends from the end portion of the guide chamfer portion in a direction away from the annular ring. In at least one embodiment of the second aspect of the present utility model, an included angle between the annular ring and the guide chamfer portion is in a range of 30-45 degrees.

In at least one embodiment of the second aspect of the present utility model, when the absorber canister is in communication with the connector, a lower surface of the lip contacts an outer sidewall of at least one port of the input port and the output port to form an annular contact surface, the width of the annular contact surface being greater than the thickness of the root portion of the lip.

In at least one embodiment of the second aspect of the present utility model, the width of the annular contact surface is between 120% and 200% of the thickness of the root portion of the at least one lip.

In at least one embodiment of the second aspect of the present utility model, the lip is made of a resilient material and the thickness of the lip tapers from the root portion to the end portion.

In at least one embodiment of the second aspect of the present utility model, the lip extends from the end portion of the guide chamfer portion in a direction towards to the annular ring. In at least one embodiment of the second aspect of the present utility model, an included angle between the annular ring and the guide chamfer portion is in a range of 45-60 degrees.

According to a third aspect of the present utility model, an anesthesia machine is provided, the anesthesia machine comprising: an absorber canister having an input port and an output port; and any connector provided according to the first or second aspect of the present utility model.

In at least one embodiment of the third aspect of the present utility model, the anesthesia machine further comprises a base, the base comprising: a lifting frame disposed below the absorber canister; and a cam disposed below the lifting frame. The lifting frame is lifted or lowered by rotating the cam, thereby inserting the input port and the output port of the absorber canister into the first and second connection ports of the connector, or withdrawing the input port and the output port of the absorber canister from the first and second connection ports of the connector.

In at least one embodiment of the third aspect of the present utility model, the lifting frame and the absorber canister are detachable.

According to a fourth aspect of the present utility model, a sealing ring is provided, the sealing ring being the seal used in any connector provided according to the first or second aspect of the present utility model.

Compared with the prior art, the technical solution proposed by the present utility model has one or a plurality of the following advantages:

(1) In some implementation manners of the present utility model, by using a lip seal and causing the width of an annular contact surface formed when a lower surface of a lip of the seal contacts a port of an absorber canister to be greater than the thickness of the root portion of the lip, a good sealing effect is obtained, and the inner diameter size of the lip is allowed to have a larger design range;

(2) In some implementation manners of the present utility model, by using the lip seal and designing the thickness of the lip to taper from the root portion to the end portion, the flexibility of the lip is improved, and the resistance received by the port of the absorber canister when it is inserted into the seal is greatly reduced;

(3) In some implementation manners of the present utility model, by sweeping an outer sidewall of the port of the absorber canister using an end portion of the lip of the seal when the absorber canister is inserted into/withdrawn from the connection port, the powder accumulated on the outer sidewall of the port of the absorber canister is removed, thereby reducing the frictional resistance received by the absorber canister when it is inserted into the seal;

(4) In some implementation manners of the present utility model, by closely attaching the lower surface of the seal lip to the outer sidewall of the port of the absorber canister, the sealing between a port of a connector and the port of the absorber canister is achieved, which provides not only good sealing performance but also self-compensation ability. The lip-shaped seal has a long service life and can be used for ten years according to reliability tests, which is sufficient to meet the service life of an anesthesia machine; and (5) In some implementation manners of the present utility model, the lip-shaped seal has a guide chamfer portion, which can guide the port of the absorber canister to be inserted to the lip of the seal without manual alignment.

BRIEF DESCRIPTION OF THE DRAWINGS

The present utility model can be better understood by describing exemplary embodiments of the present utility model with reference to accompanying drawing. In all the accompanying drawings, the same reference numerals are used to indicate the same or similar components, where.

LIST OF REFERENCE NUMERALS

Figure 1:
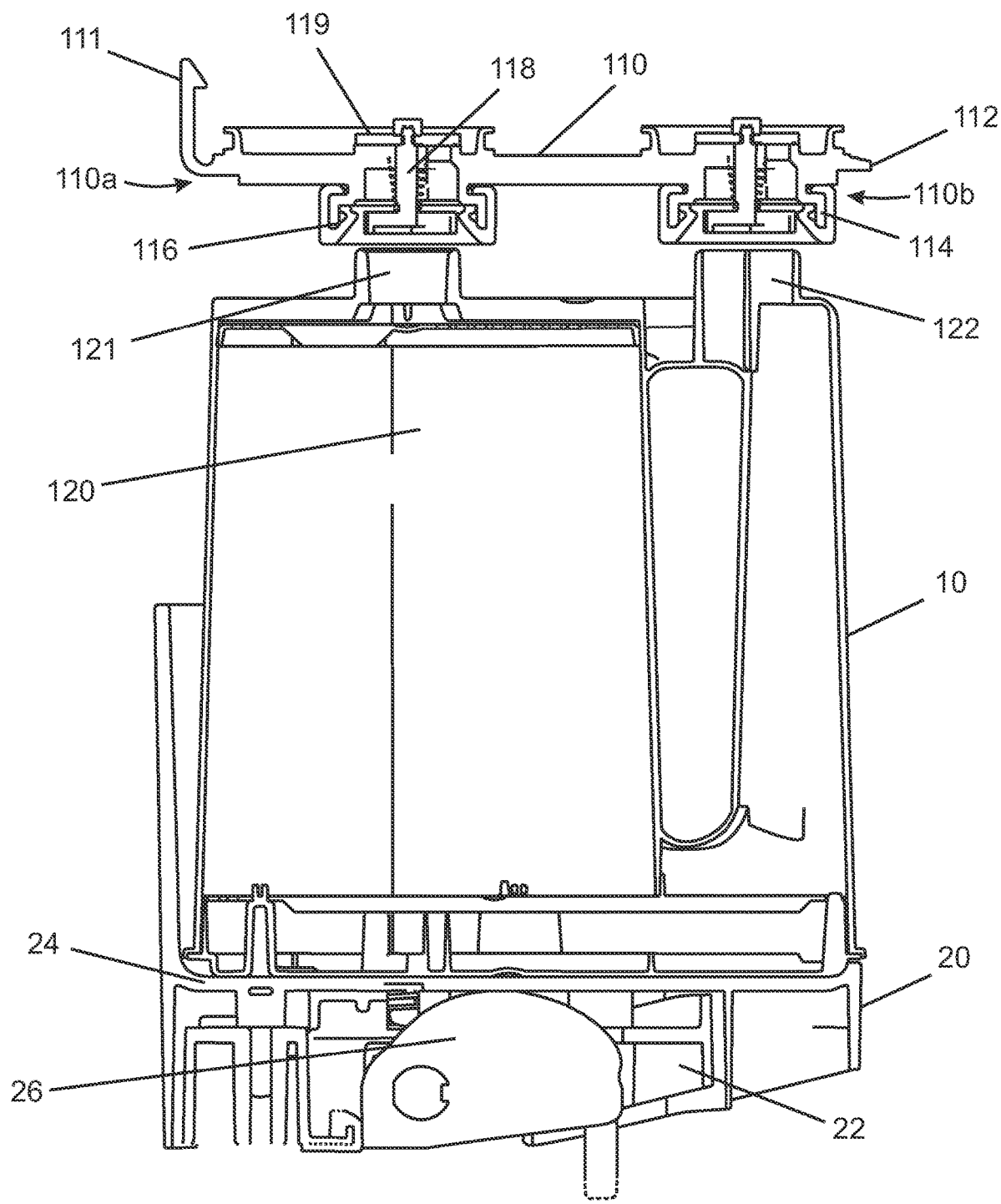
FIG. 1 is a schematic cross-sectional view of a bypass of a breathing circuit of an anesthesia machine in a non-communicating state according to an embodiment of the present utility model.

| 10 | Bypass of a breathing circuit of an anesthesia machine |
| 20 | Base |
| 22 | Base main body |
| 24 | Lifting frame |
| 26 | Cam |
| 110 | Connector |
| 111 | Gas inlet |
| 112 | Gas outlet |
| 114 | First and second connection ports |
| 116 | First and second seals |
| 116a | Annular ring |
| 116b | Lip |

-continued

| 116c | Guide chamfer portion |
| 116d | Hollow portion |
| 116e | Junction of a lip and a guide chamfer portion |
| 116f | Bend |
| 116r | Annular contact surface |
| 117 | End cover |
| 117a | Guide chamfer member |
| 118 | First and second gas valves |
| 119 | Valve cover |
| 120 | Absorber canister |
| 121 | Input port of the absorber canister |
| 122 | Output port of the absorber canister |
| A | Deformation direction of the seal |
| W | Width of the annular contact surface |
| T | Thickness of the root portion of the lip |

DETAILED DESCRIPTION

The specific implementation manners of the present utility model will be described below. It should be pointed out that, in order to provide a concise description in the specific description process of these implementation manners, it is impossible for this description to describe all features of the actual implementation manners in detail. It should be understood that in the actual implementation of any of the implementation manners, as in the process of any engineering project or design project, a variety of specific decisions are often made in order to achieve the developer's specific objectives and meet system-related or business-related restrictions, which will vary from one implementation manner to another. In addition, it should also be understood that although efforts made in this development process may be complicated and lengthy, for those of ordinary skill in the art related to the content disclosed in the present utility model, some changes in design, manufacturing, or production based on the technical content disclosed in the present disclosure are only conventional technical means and should not be understood as that content of the present disclosure is insufficient.

Unless otherwise defined, the technical or scientific terms used in the claims and the description are as they are usually understood by those of ordinary skill in the art to which the present utility model pertains. The words "first," "second" and similar words used in the description and claims of the patent application of the present utility model do not denote any order, quantity, or importance, but are merely intended to distinguish between different constituents. "One," "a" and similar words are not meant to be limiting, but rather denote the presence of at least one. The word "include," "comprise" or a similar word is intended to mean that an element or article that appears before "include" or "comprise" encompasses an element or article and equivalent elements that are listed after "include" or "comprise," and does not exclude other elements or articles. The word "connect," "connected" or a similar word is not limited to a physical or mechanical connection, and is not limited to a direct or indirect connection.

FIG. 1 is a schematic cross-sectional view of a bypass of a breathing circuit of an anesthesia machine in a non-communicating state according to an embodiment of the present utility model. As shown in FIG. 1, the bypass 10 of the breathing circuit of the anesthesia machine may include a connector 110 and an absorber canister 120. The connector 110 may include a gas inlet 111, a gas outlet 112, first and second connection ports 114, and first and second gas valves 118. The first and second connection ports 114 are substantially sleeve-shaped, each have a through hole in the middle, and are provided with first and second seals 116 on their sidewalls, respectively. The first and second connection ports 114 each have one end that can communicate with the gas inlet 111 or the gas outlet 112 and the other end being open to allow an input port 121 and an output port 122 of the absorber canister 120 to be inserted thereinto, respectively. The first and second connection ports 114 are also substantially coaxial with the first and second gas valves 118, respectively. The first and second gas valves 118 each have a valve cover 119. The first connection port 114 is on a first end portion 110a of the connector and the second connection port 114 is adjacent to a second end portion 110b, opposite from the first end portion, of the connector.

The absorber canister 120 is used for containing soda lime, and has the input port 121 and the output port 122. The absorber canister may be detachably connected to the connector 110 by its input port 121 and output port 122 being inserted into or withdrawn from the first and second connection ports 114. The absorber canister 120 may also be detachably mounted on a base 20.

The base 20 may include a base main body 22, a lifting frame 24, and a cam 26. The cam 26 can be fixed on the base main body 22 and is rotatable about a rotation axis.

In this embodiment, as shown in FIG. 1, an operator rotates the cam 26 clockwise about the rotation axis, and the lifting frame 24 and the absorber canister 120 mounted on the lifting frame 24 are lowered accordingly. Accordingly, the input port 121 and the output port 122 of the absorber canister 120 are withdrawn from the first and second connection ports 114, so that the connector 110 and the absorber canister 120 are in a non-communicating state. At this time, the operator can detach the absorber canister 120 from the base 20 to replace the absorber canister with a new one.

At the same time, since the input port 121 and the output port 122 of the absorber canister 120 are withdrawn from the first and second connection ports 114, the valve covers 119 on the first and second gas valves 118 are respectively lowered to just block passages between the connector and the main body of the breathing circuit of the anesthesia machine respectively, thus preventing $CO_2$ gas in the main body of the breathing circuit of the anesthesia machine from leaking into an operating room when the absorber canister 120 is replaced.

Figure 2:
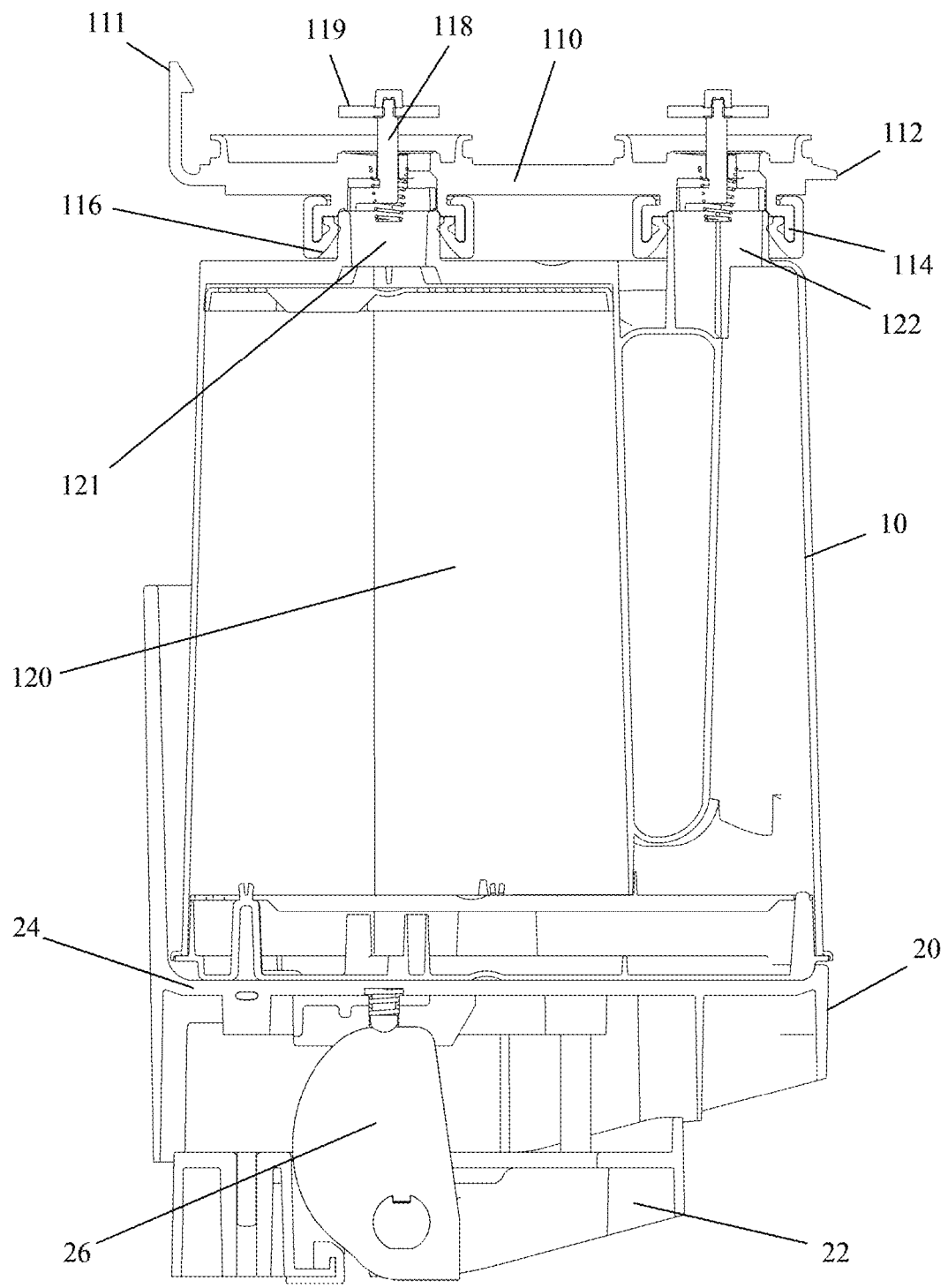
FIG. 2 is a schematic cross-sectional view of a bypass circuit of a breathing circuit of an anesthesia machine in a communicating state according to an embodiment of the present utility model.

FIG. 2 is a schematic cross-sectional view of a bypass of a breathing circuit of an anesthesia machine in a communicating state according to an embodiment of the present utility model. Similar to the structure illustrated in FIG. 1, the bypass 10 of the breathing circuit of the anesthesia machine may include a connector 110 and an absorber canister 120. When an operator rotates a cam 26 counterclockwise, a lifting frame 24 and the absorber canister 120 mounted on the lifting frame 24 are lifted accordingly. Accordingly, an input port 121 and an output port 122 of the absorber canister 120 are inserted into first and second connection ports 114, respectively. First and second seals 116 positioned on sidewalls of the first and second connection ports 114 seal gas flow between the first and second connection ports 114 and the input/output ports 121 and 122 of the absorber canister, respectively, thus avoiding gas in the connector 110 from leaking into the operating room during an operation.

At the same time, since the input port 121 and the output port 122 of the absorber canister 120 are inserted into the first and second connection ports 114 respectively, valve covers 119 on the first and second gas valves 118 are pushed upwards respectively, so that passages between the connector and a main body of the breathing circuit of the anesthesia machine are opened, and the main body of the breathing circuit of the anesthesia machine and the absorber canister 120 are in a communicating state. In the communicating state, carbon dioxide exhaled by a patient enters from the gas inlet 111 of the connector 110, passes through the first connection port 114, and enters the absorber canister 120 through the input port 121 of the absorber canister 120. In the absorber canister 120, the carbon dioxide and soda lime chemically react to produce water, heat, and a mixed gas containing $CaCO_3$, $Na_2CO_3$, and the like. The heavier water sinks to the bottom of the absorber canister 120, and the mixed gas generated by the reaction passes through the output port 122 of the absorber canister 120, enters the connector 110 through the second connection port 114, and then is discharged from the gas outlet 112.

In some embodiments, as shown in FIG. 1 and FIG. 2, the absorber canister 120 has the input port 121 and the output port 122 that are disposed separately from each other. The carbon dioxide gas exhaled by the patient enters the absorber canister 120 through the input port 121, chemically reacts with the soda lime (mainly composed of calcium hydroxide and sodium hydroxide) contained in the absorber canister 120, and at the same time releases water and heat. The mixed gas generated by the reaction is discharged from the absorber canister 120 through the output port 122. In other embodiments, the input port and the output port of the absorber canister may be disposed in a coaxial nested structure, or the input port is disposed inside the output port, or the output port is disposed inside the input port. In this case, the first and second connection ports of the connector 110 may also be disposed in a coaxial nesting structure to adapt to the coaxially disposed input port and output port.

In some embodiments, as shown in FIG. 1 and FIG. 2, seals 116 may be disposed on sidewalls of the first and second connection ports 114 so as to obtain an effective sealing between the input port 121 and output port 12 of the absorber canister 120 and the first and second connection ports 114 of the connector 110. In some implementation manners, the seal 116 may be a sealing ring.

Specific implementation manners of the seal 116 will be described below with reference to FIG. 3 to FIG. 10.

First Embodiment

Figure 3:
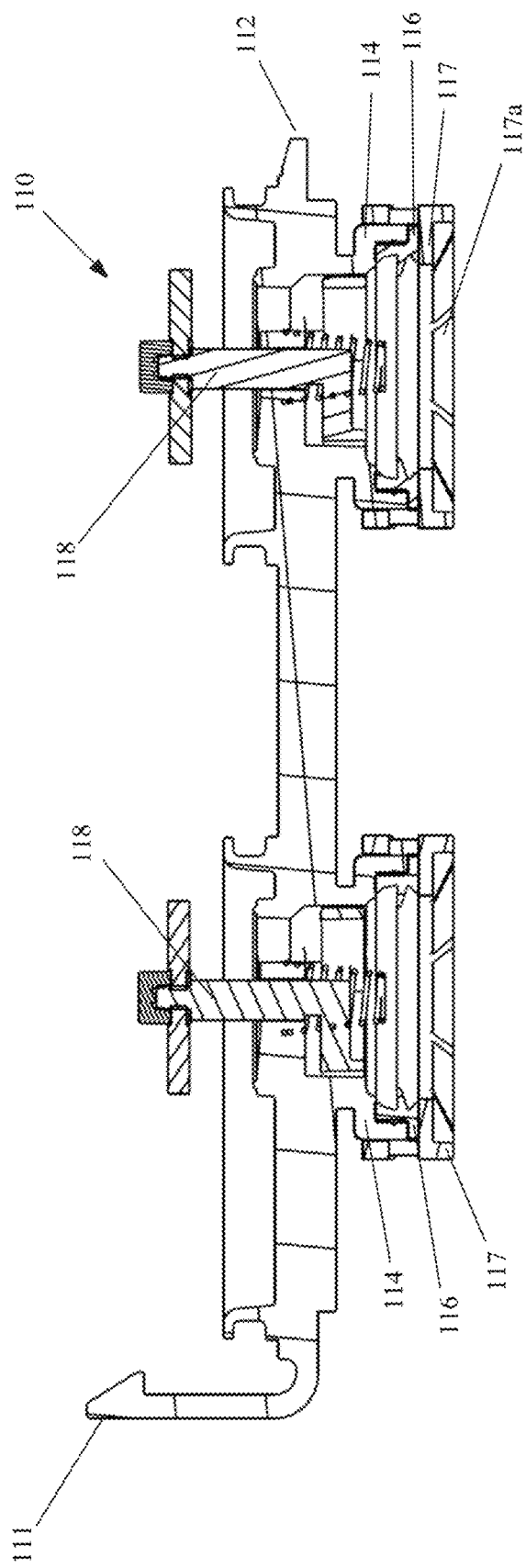
FIG. 3 is a schematic cross-sectional view of a connector in a breathing circuit of an anesthesia machine according to an embodiment of the present utility model.

FIG. 3 is a schematic cross-sectional view of a connector in a breathing circuit of an anesthesia machine according to an embodiment of the present utility model. Similar to that shown in FIG. 1 and FIG. 2, in this embodiment, the connector 110 includes a gas inlet 111, a gas outlet 112, first and second connection ports 114, and first and second gas valves 118. The first and second connection ports 114 are substantially sleeve-shaped, each have a through hole in the middle, and are provided with first and second seals 116 on their inner sidewalls, respectively. One end of the first connection port 114 on the left side can communicate with the gas inlet 111, and one end of the first connection port 114 on the right side can communicate with the gas outlet 112. The other ends of the two connection ports are open, respectively allowing the input port 121 and the output port 122 of the absorber canister 120 to be inserted thereinto from bottom to top. As shown in FIG. 3, in this embodiment, the first and second seals 116 may be lip-shaped seals. In some implementation manners, the first and second seals 116 adopt single-lip seals. The single-lip seal has a simple structure, uses less material, and is easy to manufacture and form. Moreover, the single-lip seal 116 can be directly attached to an inner sidewall of the connection port 114, which takes up very little space and is easy to replace. In some other implementation manners, the first and second seals 116 may be seals with two or more lips.

After the lip-shaped seal 116 is placed in the connection port 114, an end cover 117 can be rotated to limit the lip-shaped seal 116 in the connection port 114. In some implementation manners, a guide chamfer member 117a may be further disposed on the end cover 117, for guiding the input port 121 and the input port 122 of the absorber canister 120 into the first and second seals 116, respectively. The guide chamfer member 117a may be a component separate from the end cover 117, or may be integrally formed with the end cover 117.

Figure 4:
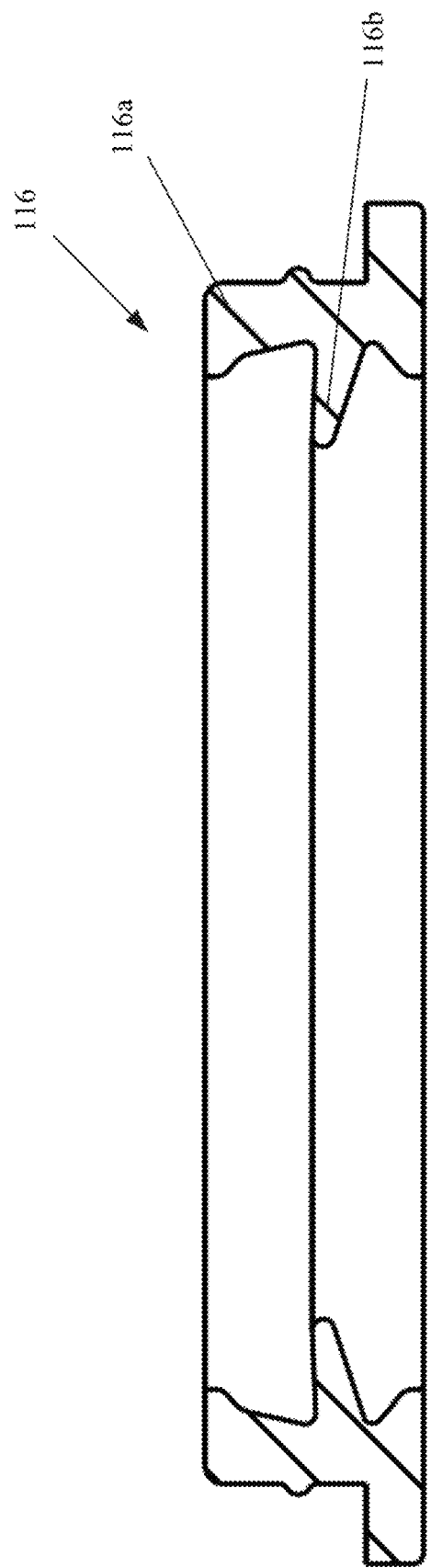
FIG. 4 is a cross-sectional view of a lip-shaped seal according to an embodiment of the present utility model.

FIG. 4 is a cross-sectional view of a lip-shaped seal according to an embodiment of the present utility model. In this embodiment, as shown in FIG. 4, the lip-shaped seal 116 is a single-lip seal. The lip-shaped seal 116 includes an annular ring 116a and a lip 116b. The annular ring 116a has a certain height. After mounting, an outer sidewall of the annular ring 116a fits an inner sidewall of the connection port 114. The lip 116b is also annular, and extends from an inner side of the annular ring 116a in a direction away from the annular ring, for example, extends substantially inwards in a radial direction. In some implementation manners, the lip 116b may be disposed near a middle portion in a height direction of the annular ring. In some other implementation manners, the lip 116b may be disposed at a position below the middle portion in the height direction of the annular ring.

In this embodiment, the inner diameter of the lip 116b may be set to be smaller than the diameter of an outer sidewall of the input port or output port of the absorber canister. In some implementation manners, the lip-shaped seal 116 may be made of a resilient material such as silicone rubber. The resilience of the lip 116b enables the input port 121 and the output port 122 of the absorber canister 120 to receive less resistance when inserted into the first and second connection ports 114, respectively. In some other implementation manners, the lip-shaped seal 116 may be made of a high temperature-resistant resilient material.

In some implementation manners, the lip 116b may be set to have a uniform thickness in the height direction of the annular ring 116a. In some other implementation manners, the lip 116b may be set to have a greater thickness at the root portion than that at the end portion. For example, the lip thickness of the lip 116b tapers as a distance from the inner side of the annular ring 116a increases. The tapered thickness of the lip 116b enables the lip to be more easily deformed. When the input port 121 and the output port 122 of the absorber canister 120 are inserted into the first and second connection ports 114, respectively, the resistances received by them will be smaller; therefore, the lip 116b can be easily pushed upwards during the insertion, so that a part of a lower surface of the lip 116b is closely attached to the outer sidewall of the input port or output port of the absorber canister.

Figure 5:
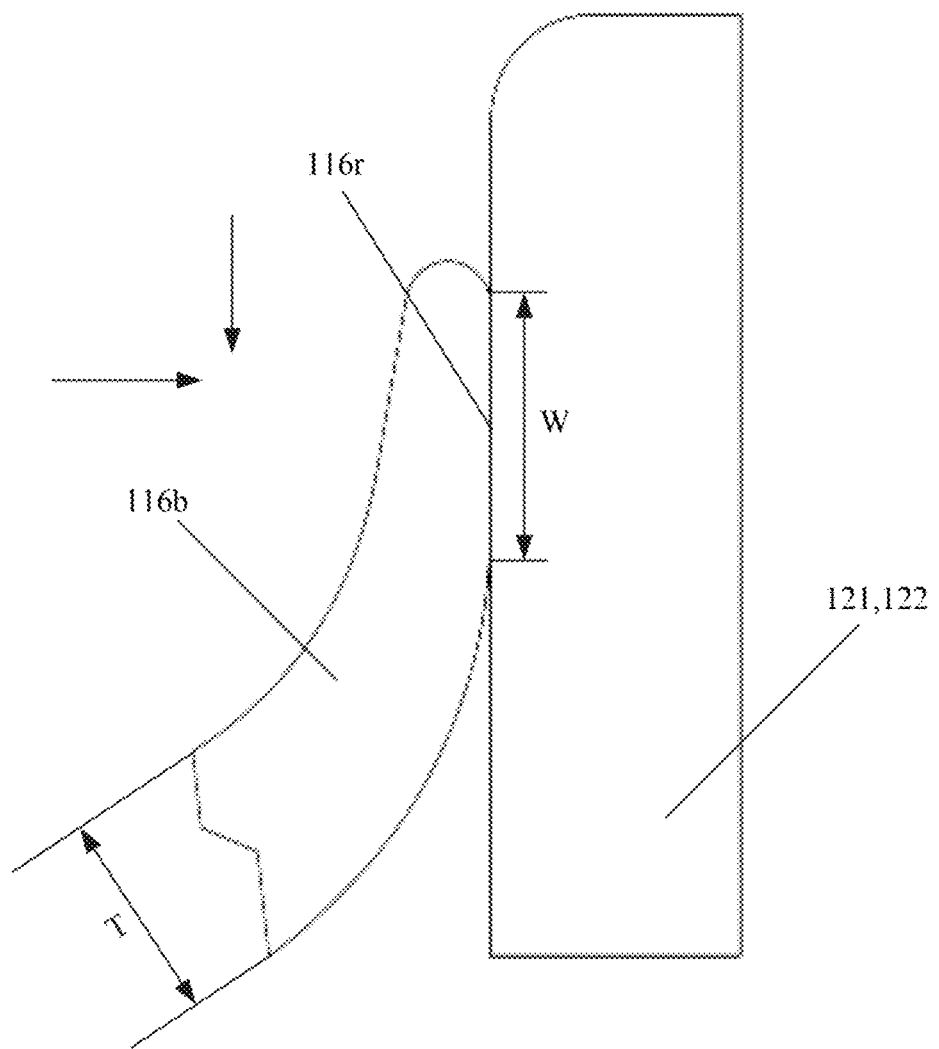
FIG. 5 is a partial enlarged view of a part of a lip of a lip-shaped seal closely attaching to an outer sidewall of a port of an absorber canister according to an embodiment of the present utility model.

FIG. 5 is a partial enlarged view of a part of a lip of a lip-shaped seal closely attaching to an outer sidewall of a port of an absorber canister according to an embodiment of the present utility model. When the input/output port 121 and 122 of the absorber canister is inserted into the corresponding connection port 114 upwards from a bottom side, since the inner diameter of the lip 116b is smaller than the diameter of outer sidewall of the input/output port 121 and 122 of the absorber canister, the input/output port 121 and 122 of the absorber canister will push the lip 116b upwards, and a part of a lower surface of the resilient lip 116b will be naturally attached to the outer sidewall of the input/output port 121 and 122. As shown in FIG. 5, when the gas pressure inside a breathing circuit is gradually increased, an upper surface of the lip 116b is not only subjected to the gas pressure from top to bottom, but also subjected to the gas pressure from left to right. The gas pressure from left to right presses the lip 116b tightly against the outer sidewall of the input/output port 121 and 122 of the absorber canister, forming a very good sealing. A greater gas pressure will result in a better sealing performance. At the same time, even if the lower surface of the lip 116b is worn due to repeated detaching of the absorber canister, under the effect of the gas pressure, the lip 116b can still be closely attached to the outer sidewall of the input/output port of the absorber canister. Therefore, the lip-shaped seal has the self-compensation ability and a long service life.

In this embodiment, a portion where the lower surface of the lip 116b contacts the outer sidewall of the input/output port of the absorber canister forms an annular contact surface 116r. In some implementation manners, the width W of the annular contact surface 116r is greater than the thickness T of the root portion of the lip 116b. The lip 116b having a larger annular contact area can obtain a better sealing effect. In some implementation manners, the width W of the annular contact surface may be set to be between 120% and 200% of the thickness T of the root portion of the lip. In some other implementation manners, the width W of the annular contact surface may be set to be between 140% and 180% of the thickness T of the root portion of the lip. In still other implementation manners, the width W of the annular contact surface may be set to be about 160% of the thickness T of the root portion of the lip.

When the input/output ports 121 and 122 of the absorber canister are inserted into the corresponding first and second connection ports 114 upwards from the bottom side or are withdrawn therefrom, an end portion of the lip 116b can sweep away a part of powder accumulated on the outer sidewalls of the input/output ports of the absorber canister, thus reducing the frictional resistances received by the input/output ports of the absorber canister when inserted into the first and second connection ports, and improving dynamic sealing of the seal in the breathing circuit of the anesthesia machine.

In a preferred implementation manner of the lip-shaped seal 116, the lip-shaped seal 116 may include only one lip 116b, which is disposed near a middle portion in a height direction of an annular ring 116a, and extends substantially in a radial direction towards an interior of the annular ring. The lip 116b is made of a resilient material, and during use, a lower surface thereof contacts the input/output port of the absorber canister to form an annular contact surface 116r. The width W of the annular contact surface 116r is greater than the thickness T of the root portion of the lip 116r. For example, the width W of the annular contact surface is between 120% and 200% of the thickness T of the root portion of the lip. The single-lip seal constructed as such has a soft lip and is easy to deform. When the input/output port 121 and 122 of the absorber canister is inserted into the lip-shaped seal 116, the resistance (including frictional resistance) applied by the lip 116b to the input/output port of the absorber canister is minimal, and the sealing performance is very good. According to tests, the single-lip seal is sufficient to meet requirements on resistance and sealing.

In other implementation manners, the lip-shaped seal 116 may be a lip-shaped seal with two or more lips. The two or more lips may be distributed in the height direction of the annular ring as needed. In some implementation manners, each of the two or more lips has a uniform thickness. The two or more lips may have the same or different thicknesses. In some other implementation manners, at least one of the two or more lips has a greater thickness at the root portion than that at the end portion. For example, the thickness of at least one lip tapers as a distance from the inner side of the annular ring 116a increases.

Second Embodiment

Figure 6:
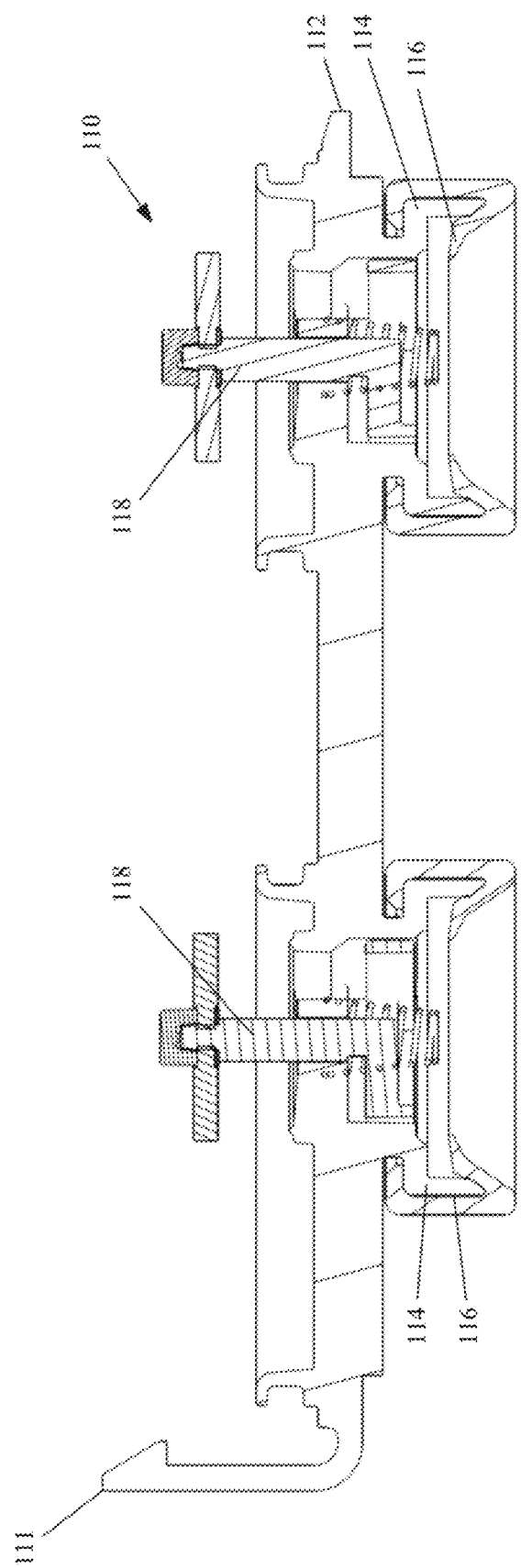
FIG. 6 is a schematic cross-sectional view of a connector in a breathing circuit of an anesthesia machine according to another embodiment of the present utility model.

FIG. 6 is a schematic cross-sectional view of a connector in a breathing circuit of an anesthesia machine according to another embodiment of the present utility model. Similar to the structure shown in FIG. 3, in this embodiment, the connector 110 includes a gas inlet 111, a gas outlet 112, first and second connection ports 114, and first and second gas valves 118. The first and second connection ports 114 are substantially sleeve-shaped, each have a through hole in the middle, and are provided with first and second seals 116 on their sidewalls, respectively. One end of the first connection port 114 on the left side can communicate with the gas inlet 111, and one end of the first connection port 114 on the right side can communicate with the gas outlet 112. The other ends of the two connection ports are open, respectively allowing the input port 121 and the output port 122 of the absorber canister 120 to be inserted thereinto from bottom to top. As shown in FIG. 6, in this embodiment, the first and second seals 116 are also lip-shaped seals, but their shapes and mounting manners are different from those of the lip-shaped seals in the first embodiment shown in FIG. 3.

Figure 7:
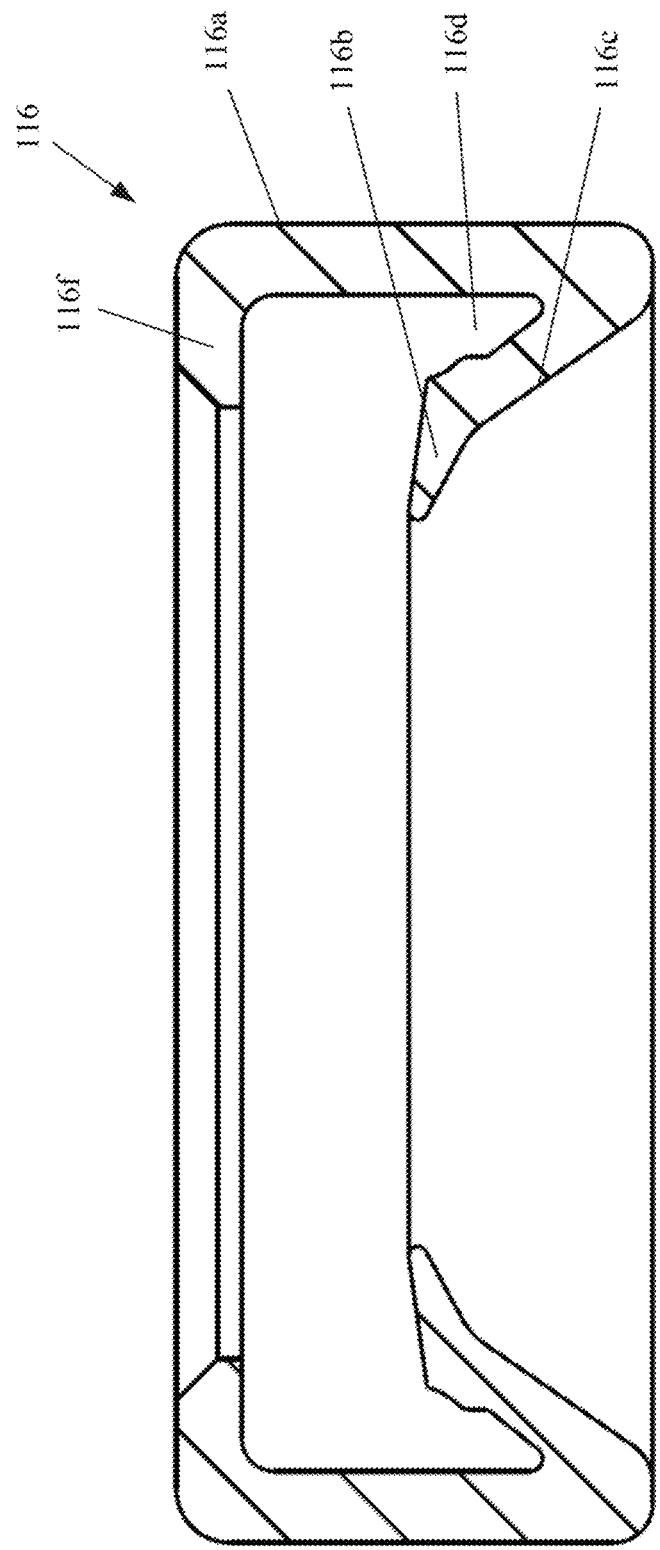
FIG. 7 is a cross-sectional view of a lip-shaped seal having a hollow portion according to another embodiment of the present utility model.

FIG. 7 is a cross-sectional view of a lip-shaped seal having a hollow portion according to another embodiment of the present utility model. In this embodiment, the lip-shaped seal 116 may be a single-lip seal, or may be a seal with two or more lips. Different from the first embodiment, the lip-shaped seal 116 of this embodiment may also include a guide chamfer portion 116c and a bend 116f in addition to the annular ring 116a and the lip 116b. The guide chamfer portion 116c may be disposed between the annular ring 116a and the lip 116b, and the bend 116f may be disposed at the top portion of the annular ring 116a. The guide chamfer portion 116c and the bend 116f may be integrally formed with the annular ring 116a and the lip 116b. In some implementation manners, the guide chamfer portion 116c is also annular, and extends obliquely inwards and upwards from the bottom of an inner side of the annular ring 116a. The lip 116b extends continuously from an end portion of the guide chamfer portion 116c in a direction away from the annular ring, for example, extends substantially inwards in a radial direction. The bend 116f extends from the top of the annular ring 116a in a direction away from the annular ring 116a, for example, extends substantially inwards in the radial direction. As shown in FIG. 7, an included angle is formed between the annular ring 116a and the guide chamfer portion 116c. After mounting, at least a part of inner sidewalls of the annular ring 116a and the bend 116f fits the outer sidewall of the connection port 114. The connection port 114 is positioned in a hollow portion 116d enclosed by the bend 116f, the annular ring 116a, the guide chamfer portion 116c, and the lip 116b. In some implementation manners, the included angle between the annular ring 116a and the guide chamfer portion 116c is in a range of 30-45 degrees.

In some implementation manners, the lip 116b may be disposed near a middle portion in a height direction of the annular ring. In some other implementation manners, the lip 116b may be disposed at a position below the middle portion in the height direction of the annular ring.

In this embodiment, the lip 116b may be set to have the same features as the lip 116b of the first embodiment, thereby having similar performance advantages. In addition, compared with the lip-shaped seal of the first embodiment, the guide chamfer portion 116c of the lip-shaped seal 116 of this embodiment can also guide the input/output port of the absorber canister to the lip 116b of the lip-shaped seal 116 when the input/output port of the absorber canister is inserted into the corresponding connection port 114, so that the guide chamfer portion 117a in the first embodiment shown in FIG. 3 can be omitted.

Third Embodiment

Figure 8:
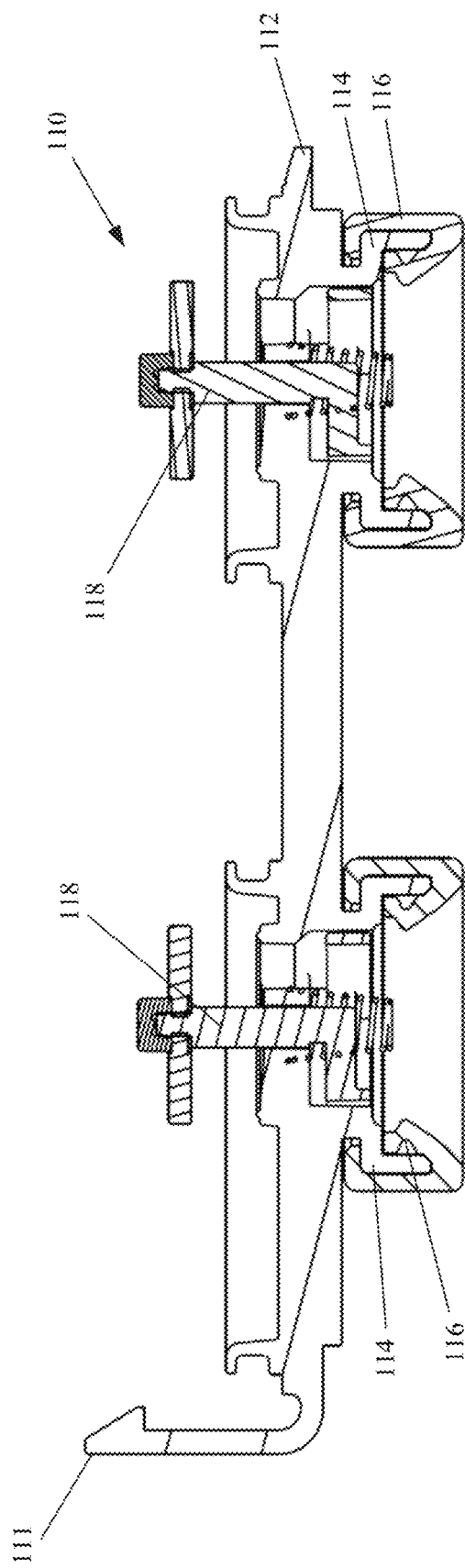
FIG. 8 is a schematic cross-sectional view of a connector in a breathing circuit of an anesthesia machine according to still another embodiment of the present utility model.

FIG. 8 is a schematic cross-sectional view of a connector in a breathing circuit of an anesthesia machine according to still another embodiment of the present utility model. Similar to the structure shown in FIG. 6, in this embodiment, the connector 110 includes a gas inlet 111, a gas outlet 112, first and second connection ports 114, and first and second gas valves 118. The first and second connection ports 114 are substantially sleeve-shaped, each have a through hole in the middle, and are provided with first and second seals 116 on sidewalls, respectively. One end of the first connection port 114 on the left side can communicate with the gas inlet 111, and one end of the first connection port 114 on the right side can communicate with the gas outlet 112. The other ends of the two connection ports are open, respectively allowing the input port 121 and the output port 122 of the absorber canister 120 to be inserted thereinto from bottom to top. As shown in FIG. 8, in this embodiment, the first and second seals 116 are lip-shaped seals having a hollow portion, and the shape thereof is slightly different from that of the lip-shaped seal in the second embodiment shown in FIG. 6.

Figure 9:
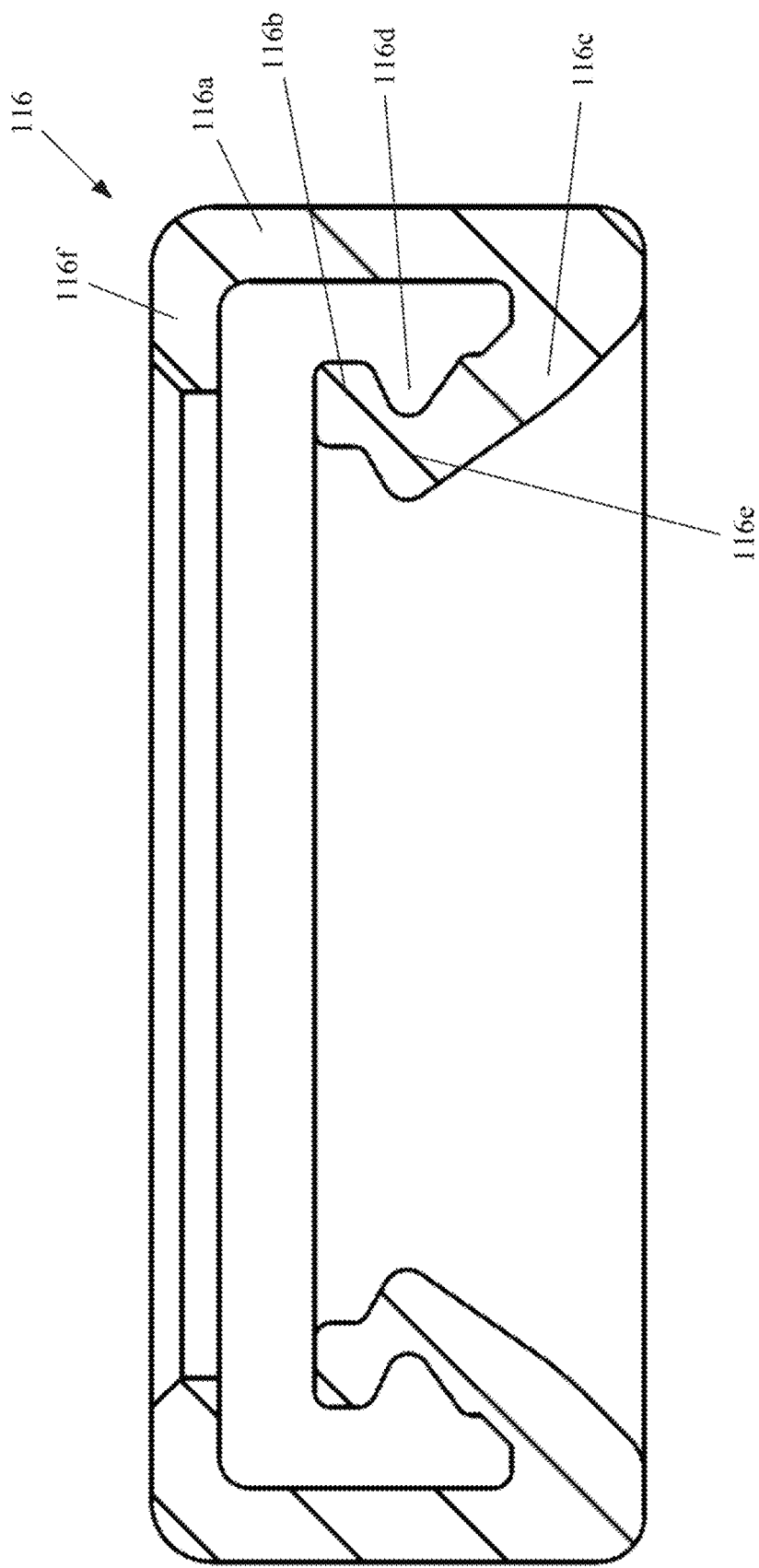
FIG. 9 is a cross-sectional view of a lip-shaped seal having a hollow portion according to still another embodiment of the present utility model.

FIG. 9 is a cross-sectional view of a lip-shaped seal having a hollow portion according to still another embodiment of the present utility model. In this embodiment, the lip-shaped hollow seal 116 includes an annular ring 116a, a lip 116b, a guide chamfer portion 116c, and a bend 116f. The guide chamfer portion 116c may be disposed between the annular ring 116a and the lip 116b, and the bend 116f may be disposed at the top portion of the annular ring 116a. The guide chamfer portion 116c and the bend 116f may be integrally formed with the annular ring 116a and the lip 116b. In some implementation manners, the guide chamfer portion 116c is also annular, and extends obliquely inwards and upwards from the bottom of an inner side of the annular ring 116a. The lip 116b extends from an end portion of the guide chamfer portion 116c in a direction towards the annular ring 116a. The bend 116f extends from the top of the annular ring 116a in a direction away from the annular ring 116a, for example, extends substantially inwards in a radial direction. As shown in FIG. 9, an included angle is formed between the annular ring 116a and the guide chamfer portion 116c. After mounting, at least a part of inner sidewalls of the annular ring 116a and the bend 116f fits the outer sidewall of the connection port 114. The connection port 114 is positioned in a hollow portion 116d enclosed by the bend 116f, the annular ring 116a, the guide chamfer portion 116c, and the lip 116b. In some implementation manners, the included angle between the annular ring 116a and the guide chamfer portion 116c is in a range of 45-60 degrees. In some implementation manners, a junction 116e of the lip 116b and the guide chamfer portion 116c may be disposed near a middle portion in a height direction of the annular ring. In some other implementation manners, the junction 116e of the lip 116b and the guide chamfer portion 116c may be disposed at a position below the middle portion in the height direction of the annular ring.

In this embodiment, the junction 116e of the lip 116b and the guide chamfer portion 116c may be set to have a minimum inner diameter, and the minimum inner diameter is smaller than the diameter of the outer sidewall of the input/output port of the absorber canister. The lip-shaped seal 116 may be made of a resilient material the same as or similar to that in the first or second embodiment.

Figure 10:
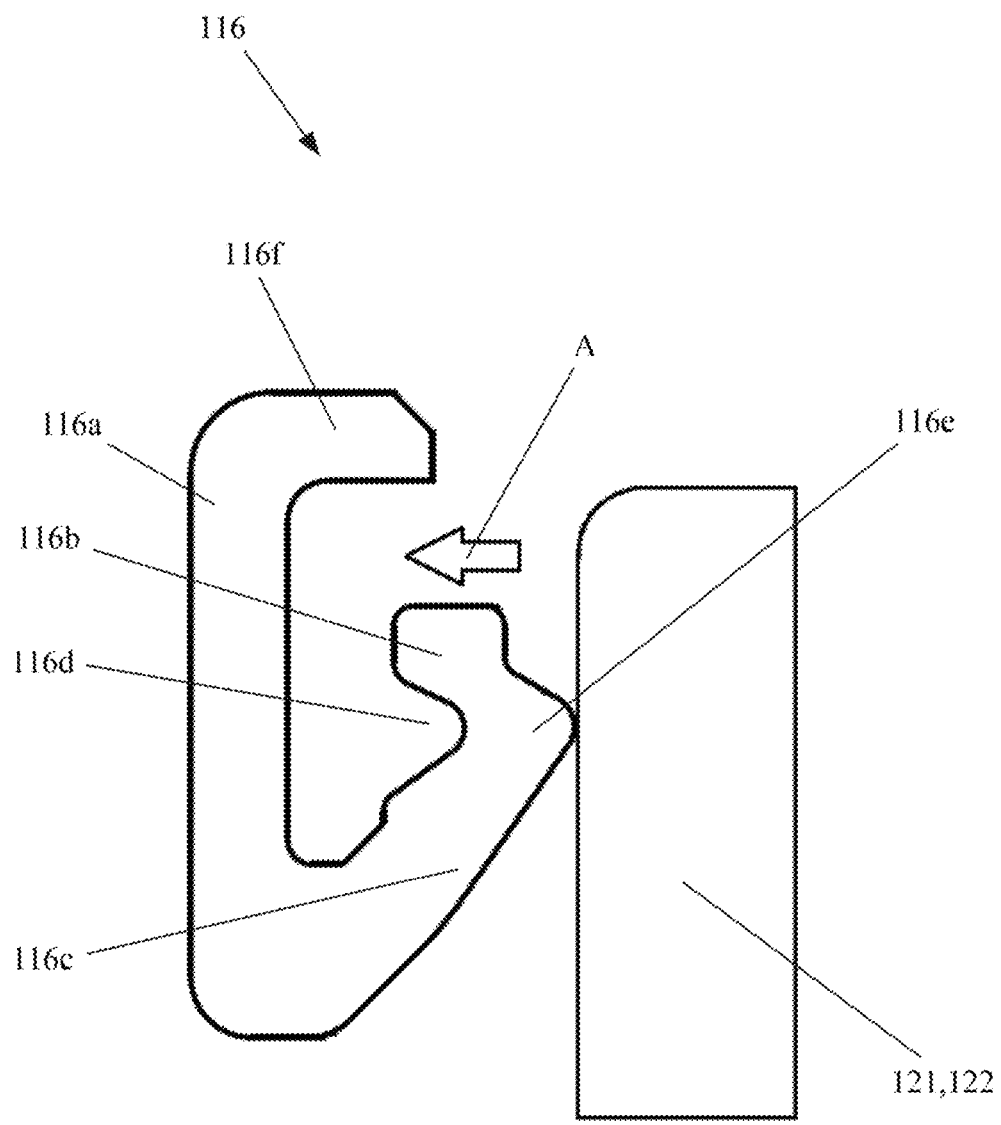
FIG. 10 is a partial enlarged view of a lip-shaped seal having a hollow portion pressing against an outer sidewall of a port of an absorber canister according to still another embodiment of the present utility model.

FIG. 10 is a partial enlarged view of a lip-shaped seal with a hollow portion pressing against an outer sidewall of a port of an absorber canister according to still another embodiment of the present utility model. Similar to the case shown in FIG. 5, when the gas pressure inside a breathing circuit is gradually increased, gas in a hollow portion 116d applies a pressure to an inner surface of a guide chamfer portion 116c. The pressure and a hollow stable structure of the lip-shaped hollow seal 116 enable a junction of a lip 11b and a guide chamfer portion 116c to tightly press against an outer sidewall of an input/output port of the absorber canister, thus forming a very good sealing. A greater gas pressure will result in a better sealing performance. A smaller minimum inner diameter at the junction of the lip 11b and the guide chamfer portion 116c compared with the outer diameter of the port of the absorber canister will result in a better sealing performance. At the same time, even if the junction of the lip 116b and the guide chamfer portion 116c is worn due to repeated detaching of the absorber canister, the resilience of the hollow structure can still enable the junction to press against the outer sidewall of the input/output port of the absorber canister. Therefore, the lip-shaped hollow seal has the self-compensation ability and a long service life.

The lip-shaped hollow seal 116 has a hollow structure so that the seal has a larger resilient range in the radial direction. In one aspect, when the input/output port of the absorber canister is inserted into the corresponding first and second connection ports 114 upwards from a bottom side, the hollow structure makes it easier for the seal 116 to be compressed in an A direction, and therefore, the resistance received by the input/output port of the absorber canister will be smaller. In another aspect, after insertion, the resilience of the hollow structure allows the junction 116e of the lip 116b and the guide chamfer portion 116c to press tightly against the outer sidewall of the input/output port of the absorber canister to implement a good sealing. In yet another aspect, even if the resilience of the hollow structure is deteriorated due to long-term use, when the outer sidewall of the input/output port of the absorber canister presses the seal outwards in a radial direction so that the lip 116b is pressed against an inner sidewall of the connection port 114, the inner sidewall of the connection port 114 will prevent the seal 116 from further deforming, and at the same time apply the same reaction force to the outer sidewall of the input/output port of the absorber canister, thus ensuring a good sealing performance.

In this embodiment, only the junction of the lip 116b and the guide chamfer portion 116c is in contact with the outer sidewall of the input/output port of the absorber canister, and the contact area is small. Therefore, when the input/output ports of the absorber canister are inserted into the corresponding first and second connection ports upwards from the bottom side, the frictional resistances received by the input/output ports of the absorber canister are smaller. In addition, similar to the guide chamfer portion in the second embodiment, the guide chamfer portion 116d of this embodiment can guide the input/output port 121 and 122 of the absorber canister to the junction with the lip 116b when the input/output port 121 and 122 of the absorber canister is inserted into the corresponding connection port 114, so that the guide chamfer member 117a in the first embodiment shown in FIG. 3 can be omitted.

Some exemplary embodiments have been described above. However, it should be understood that various modifications can be made. For example, if the described techniques are performed in a different order and/or if the components of the described system, architecture, device, or circuit are combined in other manners and/or replaced or supplemented with additional components or equivalents thereof, a suitable result can be achieved. Accordingly, other implementation manners also fall within the protection scope of the claims.

The invention claimed is:

1. A connector for connecting with an absorber canister, comprising:
   a first connection port for detachably communicating with an input port of the absorber canister;
   a second connection port for detachably communicating with an output port of the absorber canister
   wherein the first connection port is on a first end portion of the connector and the second connection port is adjacent to a second end portion, opposite from the first end portion, of the connector; and
   a seal, the seal being sleeved on a sidewall of each of the first connection port and the second connection port, and the seal comprising:
   an annular ring positioned on an outer surface of the sidewall of each of the connection ports; a guide chamfer portion, the guide chamfer portion being annular and extending obliquely from a bottom of the annular ring towards an interior of the connection ports; and
   a lip, the lip being annular and extending from an end portion of the guide chamfer portion in a direction towards the annular ring, wherein an annular hollow portion is formed between the annular ring and the guide chamfer portion, and the sidewall of each of the connection ports is positioned in the hollow portion, and wherein the seal further comprises a bend, the bend extending substantially inwards from a top portion of the annular ring in a radial direction away from the annular ring.

2. The connector according to claim 1, wherein an included angle between the annular ring and the guide chamfer portion is in a range of 45-60 degrees.

3. The connector according to claim 1, wherein, when the absorber canister is in communication with the connector, a junction of the lip and guide chamfer portion contacts an outer sidewall of at least one port of the input port and the output port to form an annular contact surface.

4. The connector according to claim 3, wherein the junction is made of a resilient material.

* * * * *